United States Patent [19]

Takahara et al.

[11] 4,082,752

[45] Apr. 4, 1978

[54] PROCESS FOR FLUORINATION OF URACIL

[75] Inventors: Takao Takahara, Mishima; Susumu Misaki, Minoo, both of Japan

[73] Assignee: Daikin Kogyo Co., Ltd., Osaka, Japan

[21] Appl. No.: 792,223

[22] Filed: Apr. 29, 1977

[30] Foreign Application Priority Data

Apr. 29, 1976 Japan .................................. 51-49163

[51] Int. Cl.$^2$ ........................................... C07D 239/54
[52] U.S. Cl. ................................................... 260/260
[58] Field of Search ......................................... 260/260

[56] References Cited

U.S. PATENT DOCUMENTS 3,682,917  8/1972  Knuniants et al. .................... 260/260
3,954,758  5/1976  Schuman et al. ..................... 260/260

Primary Examiner—Paul M. Coughlan, Jr.
Attorney, Agent, or Firm—Birch, Stewart, Kolasch and Birch

[57] ABSTRACT

An improved process for fluorination of uracil, which comprises treating uracil with fluorine which is optionally diluted with an inert gas (e.g. nitrogen gas) at a temperature of −10° to 15° C in a 50 to 85% by weight aqueous solution of hydrofluoric acid as the reaction medium to form 5-fluorouracil, and optionally subjecting the reaction mixture to a heat treatment at a temperature higher than the reaction temperature, to give 5-fluorouracil in a high yield.

10 Claims, No Drawings

PROCESS FOR FLUORINATION OF URACIL

The present invention relates to a process for fluorination. More particularly, it relates to an improved process for flourination of uracil.

In recent years, there is an increasing demand for 5-flourouracil which is a useful compound as a carcinostatic substance by itself and also as an intermediate for synthesis of other carcinostatic substances, and development of an industrially efficient process for its production is highly desired.

Among the hitherto known processes for production of 5-flourouracil, the method comprising direct flourination of uracil with flourine in an appropriately selected reaction medium is considered to be relatively profitable, and a variety of improvements have been proposed concerning this method. However, these improved processes are not sufficiently satisfying from the industrial viewpoint.

For example, the process in which the reaction of uracil with flourine is effected in a medium such as acetic acid (at 20 - 25° C), anhydrous hydrogen flouride, sulfuric acid or water (U.S. Pat. No. 3,682,917) gives a low yield and requires a long time for completion of the reaction. Besides, the process efficiency is not good because of the small concentration of uracil in the reaction medium. Particularly, as shown in Example 2 of the above U.S. Patent, when the reaction is carried out in anhydrous hydrogen fluoride at 0° to 5° C for 7 hours, 5-flourouracil is obtained in such a low yield as 6.1%.

As an improved method for eliminating the said disadvantages, there has been suggested a process comprising treating uracil with fluorine in glacial acetic acid as the reaction medium with vigorous stirring (Re = 35,000 - 45,000) (U.S. Pat. No. 3,846,429). This process can practically overcome the above mentioned drawbacks, but the control of the condition for stirring is difficult and, with an erroneous control, there is a risk of an explosion due to the extremely high reactivity of fluorine because uracil is in a suspended state.

As to the process in which the reaction of uracil with fluorine is effected in a medium such as water, perfluoroketone or trifluoroacetic acid (W. German Patent Offenlegungsschrift 21 49 504), the efficiency is insufficient in the case of using water as the reaction medium because of the low concentration of uracil therein and, thus, the 5-fluorouracil can be obtained only in a low yield. The use of perfluoroketone or trifluoroacetic acid as the reaction medium is economically disadvantageous because these substances are relatively expensive.

In the process comprising a reaction of uracil with fluorine in an aqueous medium in a uracil concentration of 1% by weight or more and at a reaction temperature of 9° to 100° C (U.S. Pat. No. 3,954,758), the yield of 5-fluorouracil is usually low. For instance, as shown in Example 10 of the above U.S. Patent, when the reaction is carried out at 9° - 13° C, 5-fluorouracil is obtained only in a slight amount, and in other examples wherein the reaction is carried out at a relatively high temperature (e.g. 49° to 95° C), the yield is somewhat improved but is still low. Moreover, since the reaction of uracil is carried out in a suspended state at a relatively high temperature, there is a risk of an explosion in water due to the high reactivity of fluorine. Thus, this process is not suitable as an industrial process for the production of 5-fluorouracil.

As the result of an extensive study for overcoming the said drawbacks seen in these conventional methods and for developing an industrially advantageous process for fluorination of uracil, it has now been found that 5-fluorouracil can be obtained with a good efficiency by treating uracil with fluorine directly at −10° to 15° C in an aqueous solution of hydrofluoric acid having a specific concentration of 50 to 85% by weight as the reaction medium.

According to the present invention which has been completed on the basis of this finding, there is provided a process for fluorination of uracil which comprises treating uracil with fluorine at a temperature of −10° to 15° C in a 50 to 85% by weight aqueous solution of hydrofluoric acid as the reaction medium to afford 5-fluorouracil.

In the process of the invention, the reaction of uracil with fluorine is effected in a medium having the said specific concentration and at the said specific temperature, and hence, the reaction proceeds safely under a mild condition and in a high uracil concentration to prepare the objective 5-fluorouracil in a high yield and especially with a high selectivity. In addition to such an excellent efficiency in industrial practice, the process of the invention shows also an economical advantage, because the said reaction medium having the specific concentration can be readily prepared by admixing with an appropriate amount of water anhydrous hydrogen fluoride which is available at a relatively low cost.

In the above mentioned conventional processes, it is known that, in case of using anhydrous hydrogen fluoride as the reaction medium, 5-fluorouracil can be obtained only in an extremely low yield of 6.1% by reaction at a reaction temperature of 0° to 5° C for 7 hours (see, Example 2 in U.S. Pat. No. 3,682,917). It is also known that, in case of using water as the reaction medium, only a trace amount of 5-fluorouracil can be obtained when the reaction is effected in a uracil concentration of 1% by weight at 9° to 13° C (U.S. Pat. No. 3,954,758), and, even when the reaction is effected in a uracil concentration of about 0.3% by weight at room temperature, the yield of 5-fluorouracil is still low (55%) (W. German Patent Offenlegungsschrift 21 49 504). Thus, hydrogen fluoride and water can afford, when used solely as the reaction medium at a relatively low temperature, only a low yield of 5-fluorouracil. To the contrary, it has unexpectedly been found that the combined use of them in a specific mixing proportion and at a specific temperature can afford 5-fluorouracil in such a high yield as 80% or more (cf. Examples described hereinafter). On the other hand, in case of using a mixture of trifluoroacetic acid with water as the reaction medium, the yield of 5-fluorouracil is lowered, compared with the case of the sole use of trifluoroacetic acid, as shown in the Examples described hereinafter. Thus, the effect of improvement of the yield of 5-fluorouracil by the incorporation of water is varied depending on the kind of the solvent to be admixed with water. In this respect too, the above mentioned effect exerted by the reaction medium of the invention comprising hydrogen fluoride and water should be considered as an unexpected, surprising finding.

The aqueous solution of hydrofluoric acid to be used as the reaction medium in the invention is required to have a hydrofluoric acid concentration of 50 to 85% by weight, preferably 60 to 75% by weight. When the concentration is lower than 50% by weight, the solubility of uracil as the starting material is markedly decreased, compared with the case of the concentration of 60% by weight, to make the process efficiency low. Besides, the proportion of the unreacted uracil becomes large, and the amount of by-products tends to increase with decrease of the concentration of hydrofluoric acid. When the concentration is higher than 85% by weight, to the contrary, a by-product which shows a specific absorption at 1100 cm$^{-1}$ in the IR spectrum is formed in a large amount. Since the isolation of this by-product from the objective 5-fluorouracil is relatively difficult, the efficiency in recrystallization is lowered to decrease the yield of 5-fluorouracil. In case of the concentration exceeding 75% by weight, it is desirable to select a relatively low reaction temperature, but such heat control is not only attainable with difficulty but is also disadvantageous economically.

In general, the concentration of uracil in the reaction medium of the invention is 1% by weight or more, usually 5 to 30% by weight, preferably 5 to 20% by weight. Even a uracil concentration lower than 1% by weight can afford 5-fluorouracil with a good yield, but the process efficiency is low, so that such a very low uracil concentration is practically undesirable from the industrial viewpoint.

The reaction temperature is usually −10° to 15° C. For obtaining 5-fluorouracil with a higher efficiency, a temperature of −10° to 10° C is favorable. When the reaction temperature is lower than −10° C, the reaction rate is small, and when it is higher than 15° C, a large amount of by-products is formed. In both cases, therefore, the yield is decreased. In general, the yield of 5-fluorouracil is largely dependent upon the concentration of hydrofluoric acid in the aqueous solution of hydrofluoric acid and the reaction temperature. It is thus required to select an appropriate temperature from the said temperature range depending on the concentration of hydrofluoric acid selected in the above mentioned range of concentration.

In effecting the process of the invention, uracil is dissolved in the 50 to 85% by weight aqueous solution of hydrofluoric acid, and fluorine gas is introduced therein with stirring to cause the fluorination. It is desired to dilute the fluorine gas with an inert gas for avoiding a rapid progress of the reaction. For instance, the fluorine gas is admixed with nitrogen gas in an amount of about 0 to 3 times (by volume) of that of the fluorine gas.

As to the following amount of the fluorine gas, there is not any particular limitation, but it is favorable to appropriately control the velocity of its introduction for preventing decomposition of the starting uracil and the produced 5-fluorouracil due to the heat generation in the fluorination of uracil.

The amount of fluorine is usually desired to be equimolar with respect to the uracil or larger for completing the fluorination. Preferably, 1.0 to 1.5 moles of fluorine are used to 1 mole of uracil.

After the fluorination is completed, the introduction of the fluorine gas is stopped, and nitrogen gas is made to pass through the reaction mixture for a while to remove the volatile components present in the reaction system. Then, the reaction medium is distilled off, usually at a temperature of 40° to 120° C under normal or reduced pressure, during which the reaction intermediate present in the reaction mixture is converted into the objective 5-fluorouracil.

The thus obtained crude 5-fluorouracil is optionally dissolved in an about 5 to 20 times larger amount of water with heating, and the resultant solution is filtered and cooled to obtain crystals of 5-fluorouracil with high purity.

As is understood from the above description, it is necessary, according to the process of the invention, for obtaining 5-fluorouracil with a good efficiency and with industrial advantage that the reaction of uracil with fluorine is effected at −10° to 15° C in the 50 to 85% by weight aqueous solution of hydrofluoric acid, the use of which is the characteristic feature of the invention. The combination of the aqueous solution of hydrofluoric acid having the said specific concentration and the said specific temperture shows a remarkable effect which has never been obtainable in the conventional methods. Thus, the present process is not only quite different in its technique and thought from the said conventional methods but also could not be anticipated therefrom.

A practical and presently preferred embodiment of the invention is illustratively shown in the following Example.

EXAMPLE

In a 200 ml volume flask made from "Daiflon Resin" (trifluorochloroethylene resin manufactured by Daikin Kogyo Co., Ltd.) which is equipped with a stirrer, a cooler, an inlet for gas and a thermometer, a designed amount of uracil and an aqueous solution of hydrofluoric acid (50 g) are charged, and the contents are stirred at a temperature lower than the reaction temperature to dissolve uracil in the aqueous solution of hydrofluoric acid. A designed amount of fluorine gas diluted or not with nitrogen gas is introduced therein over a period of 30 minutes to 1 hour. Then, nitrogen gas is made to pass through the flask for about 10 minutes to remove fluorine present in the reaction system. The reaction solvent is distilled off with heating to obtain crude 5-fluorouracil.

A sample of the thus obtained crude 5-fluorouracil is subjected to liquid chromatography to determine the contents of 5-fluorouracil and unreacted uracil by the absolute calibration curve method. The crude 5-fluorouracil is dissolved in water with heating and the resultant solution is filtered for removing insoluble materials and then cooled to obtain crystals of 5-fluorouracil, which is identified with the standard 5-fluorouracil by analysis of the IR spectrum and the UV spectrum and determination of the melting point. UV absorption spectrum: $\lambda_{max}^{pH\ 2}$: 266 mμ; $\lambda_{max}^{pH\ 10.5}$: 269 mμ. M.P.: 282° − 283° C (partially decomposed). The results are shown in Table 1.

Table 1

| No. | Medium Concent-ratio of hydrofluoric acid (% by weight) | Starting uracil Concentration of uracil in medium (% by weight) | Mol | Reaction temperature (° C) | $F_2:N_2$ (volume ratio) | $F_2$ Mol | Duration of introduction of $F_2$ (hr.) | Analysis of purity of crude product 5FU (% by weight) | Unreacted uracil (% by weight) | Selectivity of 5FU (%) | Yield of 5FU (%) | Remarks |
|---|---|---|---|---|---|---|---|---|---|---|---|---|
| 1 | 84 | 10 | 0.045 | −10 | 1:0 | 0.059 | 1 | 85.0 | 0 | 85.0 | 85.0 | Ex* |
| 2 | 60 | 10 | 0.045 | 0 | 1:0 | 0.059 | 1 | 80.5 | 8.2 | 87.7 | 80.0 | " |
| 3 | 76 | 10 | 0.045 | 0 | 1:0 | 0.059 | 1 | 80.0 | 5.0 | 84.2 | 80.2 | " |
| 4 | 84 | 10 | 0.045 | 0 | 1:1 | 0.059 | 1 | 89.9 | 1.5 | 91.3 | 82.2 | " |
| 5 | 90 | 10 | 0.045 | 0 | 1:0 | 0.059 | 1 | 71.2 | 9.2 | 78.4 | 70.0 | Compar** |
| 6 | 0 | 2 | 0.01 | 10 | 1:0 | 0.013 | 0.5 | 10.4 | 65.0 | 29.7 | 12.0 | " |
| 7 | 25 | 2 | 0.01 | 10 | 1:0 | 0.013 | 0.5 | 55.2 | 46.7 | 87.2 | 54.0 | " |
| 8 | 50 | 2 | 0.01 | 10 | 1:0 | 0.013 | 0.5 | 75.0 | 22.1 | 96.3 | 75.0 | Ex |
| 9 | 60 | 10 | 0.045 | 10 | 1:3 | 0.059 | 1 | 89.2 | 0 | 89.2 | 88.0 | " |
| 10 | 70 | 10 | 0.045 | 10 | 1:0 | 0.059 | 1 | 86.0 | 0 | 86.0 | 80.0 | " |
| 11 | 90 | 10 | 0.045 | 10 | 1:0 | 0.059 | 1 | 24.9 | 16.2 | 29.7 | 28.0 | Compar |
| 12 | 60 | 17 | 0.089 | 10 | 1:0 | 0.12 | 1 | 80.0 | 0 | 80.0 | 80.0 | Ex |
| 13 | 60 | 10 | 0.045 | 15 | 1:0 | 0.059 | 1 | 82.2 | 1.0 | 83.0 | 81.0 | " |
| 14 | 75 | 10 | 0.045 | 15 | 1:0 | 0.059 | 1 | 79.4 | 0.8 | 82.0 | 81.2 | " |
| 15 | 0 | 2 | 0.01 | 20 | 1:0 | 0.013 | 0.5 | 14.2 | 61.7 | 29.7 | 15.0 | Compar |
| 16 | 50 | 10 | 0.045 | 20 | 1:0 | 0.059 | 1 | 23.8 | 0.2 | 37.1 | 23.0 | " |
| 17 | 60 | 10 | 0.045 | 20 | 1:0 | 0.059 | 1 | 49.3 | 2.1 | 84.3 | 47.0 | " |
| 18 | 76 | 10 | 0.045 | 20 | 1:0 | 0.059 | 1 | 50.0 | 0.4 | 52.2 | 52.0 | " |

Note:
1) 5FU: 5-Fluorouracil.
2) Selectivity of 5Fu: $\dfrac{\text{5FU in crude product (\% by weight)}}{100 - (\text{unreacted uracil in crude product (\% by weight)})} \times 100$
3) Yield of 5Fu: $\dfrac{\text{(Weight of crude product (g))} \times \text{(5FU in crude product (\% by weight))}}{\text{Theoretical amount of 5FU (g)}}$
4) Ex*: Correspondong to the present Example
5) Compar**: Not corresponding to the present Example, but for comparison.

COMPARATIVE EXAMPLE

The fluorination of uracil is carried out in the same manner as in the above mentioned Example but using trifluoroacetic acid or a mixture of trifluoroacetic acid and water as the reaction medium. The results are shown in Table 2.

Table 2

| No. | Composition of medium $CF_3COOH:H_2O$ (weight ratio) | Analysis of purity of crude product 5 FU (% by weight) | Unreacted uracil (% by weight) | Yield of 5 FU (%) |
|---|---|---|---|---|
| 1 | 50 : 50 | 43 | 10 | 42.1 |
| 2 | 70 : 30 | 74.5 | 7.2 | 69.0 |
| 3 | 100 : 0 | 83.0 | 0 | 83.0 |

What is claimed is:

1. A process for fluorination of uracil which comprises treating uracil with fluorine at a temperature of −10° to 15° C in a 50 to 85% by weight aqueous solution of hydrofluoric acid as the reaction medium to form 5-fluorouracil.

2. The process for fluorination according to claim 1, wherein the concentration of uracil in the reaction medium is at least 1% by weight.

3. The process for fluorination according to claim 2, wherein the concentration of uracil in the reaction medium is in the range of 5 to 30% by weight.

4. The process for fluorination according to claim 1, wherein the hydrofluoric acid concentration is in the range of 60 to 75% by weight.

5. The process for fluorination according to claim 1, wherein the reaction temperature is in the range of −10° to 10° C.

6. The process for fluorination according to claim 1, wherein the fluorine to be used is diluted with an inert gas.

7. The process for fluorination according to claim 6, wherein the inert gas is nitrogen gas.

8. The process for fluorination according to claim 1, wherein the reaction mixture is, after completion of the fluorination, subjected to a heat treatment at a temperature higher than the reaction temperature.

9. The process for fluorination according to claim 8, wherein the heat treatment is carried out at 40° to 120° C.

10. The process for fluorination according to claim 2, wherein the concentration of uracil in the reaction medium is in the range of 5 to 20% by weight.

* * * * *